US00PP09210P

United States Patent [19]

Svejda

[11] Patent Number: Plant 9,210

[45] Date of Patent: Jul. 25, 1995

[54] SHRUB ROSE PLANT NAMED 'FRONTENAC'

[75] Inventor: Felicitas J. Svejda, Nepean, Canada

[73] Assignee: Her Majesty the Queen in right of Canada as represented by the Minister of Agriculture, Ottawa, Canada

[21] Appl. No.: 215,590

[22] Filed: Mar. 22, 1994

[51] Int. Cl.[6] ..... A01H 5/00

[52] U.S. Cl. ..... Plt./1

[58] Field of Search ..... Plt. 1, 27, 26

[56] References Cited

PUBLICATIONS

Ogilvie, et al., 1993, "'Frontenac' Rose", Hortscience 28(2):161.

*Primary Examiner*—Howard J. Locker

*Attorney, Agent, or Firm*—Burns, Doane, Swecker & Mathis

[57] ABSTRACT

A new and distinct variety of shrub rose plant is provided which forms on a repetitive basis attractive blossoms that are Roseine Purple on the upper surface and Magnolia Purple on the under surface. The new variety exhibits an upright growth habit, and good winter hardiness. Resistance to powdery mildew and blackspot has been observed. The new variety propagates well by the use of softwood stem cuttings, and is well adapted for growing as colorful ornamentation in the landscape.

4 Drawing Sheets

SUMMARY OF THE INVENTION

The new variety of shrub rose plant of the present invention was created by artificial pollination during 1981 at the Central Experimental Farm, Ottawa, Ontario, Canada. The female parent (i.e., the seed parent) was [(Queen Elizabeth×Arthur Bell)×(Red Dawn×Suzanne)], and the male parent (i.e., the pollen parent) was [(*Rosa kordesii*×(Red Dawn×Suzanne)×(Red Dawn×Suzanne)]. The Queen Elizabeth variety is the subject of U.S. Plant Pat. No. 1,259. Each of the other named plants utilized in the breeding program was non-patented in the United States. Selective study carried out at Ottawa, Ontario, Canada, resulted in the identification of a single plant of the new variety.

It was found that the new variety of shrub rose plant of the present invention possesses the following combination of characteristics:

(a) exhibits an upright growth habit,
(b) forms on a repetitive basis attractive blossoms that are Roseine Purple on the upper surface and Magnolia Purple on the under surface,
(c) propagates well by the use of softwood cuttings,
(d) exhibits a good winter hardiness, and
(e) is particularly well suited for growing in the landscape.

The rose plants can be grown well on their own roots out-of-doors without protection at L'Assomption, Quebec, Canada. Repeat flowering commonly is exhibited from approximately June to September. During the initial flowering in June, the plant commonly is almost completely covered with blossoms. Resistance to powdery mildew and blackspot is exhibited.

The new variety well meets the needs of the horticultural industry. It can be grown to advantage as attractive ornamentation in parks, gardens, public areas, and residential landscapes. It is particularly well suited for growing in the landscape.

The characteristics of the new variety have been found to be homogenous and stable and have been shown to be strictly transmissible by asexual propagation by the rooting of softwood stem cuttings and by tissue culture conducted at L'Assomption, Quebec, Canada.

The new variety has been named the Frontenac variety.

BRIEF DESCRIPTION OF THE PHOTOGRAPHS

The accompanying photographs show, as nearly true as it is reasonably possible to make the same in color illustrations of this character, typical specimens of plants and plant parts of the new variety. The rose plants of the new variety described herein were approximately 5 to 6 years of age and were photographed during September 1993 while growing on their own roots at L'Assomption, Quebec, Canada.

FIG. 1 illustrates a newly opened flower, buds, and foliage of the new variety while growing in the landscape, FIG. 2 illustrates fully opened flowers immediately prior to petal drop and foliage of the new variety while growing in the landscape, FIG. 3 illustrates a specimen of a young bud of the new variety wherein the sepals are largely open and the petals are beginning to open, FIG. 4 illustrates a specimen of a young flower of the new variety wherein the petals are in a more advanced stage of opening, FIG. 5 illustrates a specimen of a young flower of the new variety as the petals assume a further stage of opening, FIG. 6 illustrates a specimen of a flower of the new variety at a more advanced stage of opening than as illustrated in FIG. 5, FIG. 7 illustrates a specimen of a flower of the new variety at a more advanced stage of opening than as illustrated in FIG. 6, FIG. 8 illustrates a specimen of a fully open flower of the new variety, FIG. 9 illustrates on the left a specimen of a floral receptacle showing the arrangement of the stamens (sepals removed), and on the right a specimen of a floral receptacle showing the arrangement of the pistils (sepals and stamens removed), FIG. 10 illustrates a specimen of new growth of the new variety, FIG. 11 illustrates the upper surface of typical leaves of the new variety with a specimen having seven leaflets being shown on the left, a specimen having five leaflets being shown at the middle, and a specimen having three leaflets being shown on the right, and FIG. 12 illustrates the under surfaces of typical leaves of the new variety with a specimen having seven leaflets being shown on the left, a specimen having five leaflets being shown at the middle, and a specimen having three leaflets being shown on the right.

DETAILED DESCRIPTION

Figure 1:
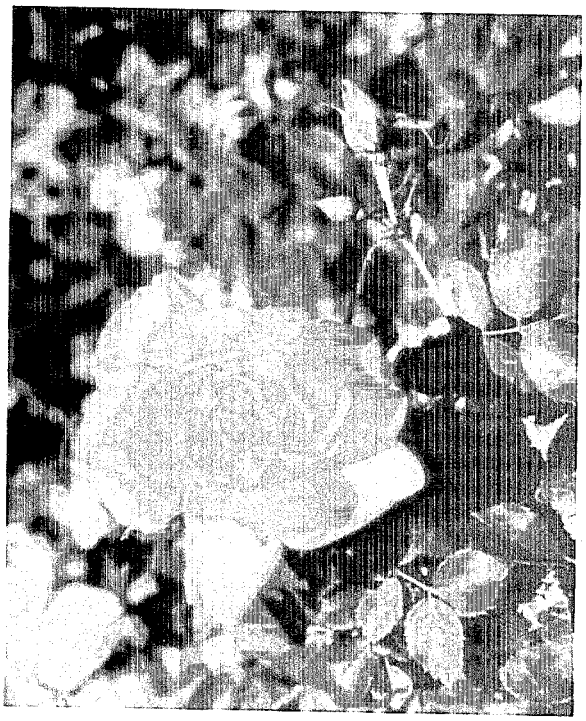
Figure 2:
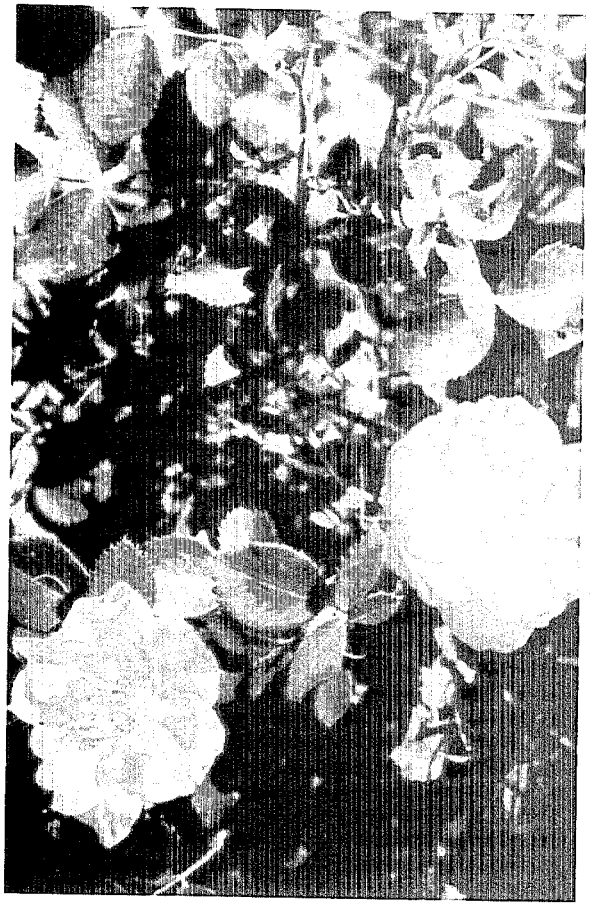
Figure 3:
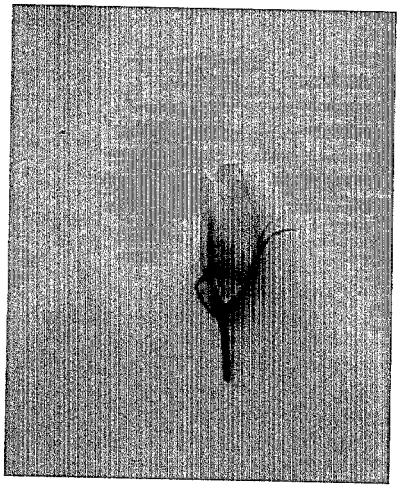
Figure 4:
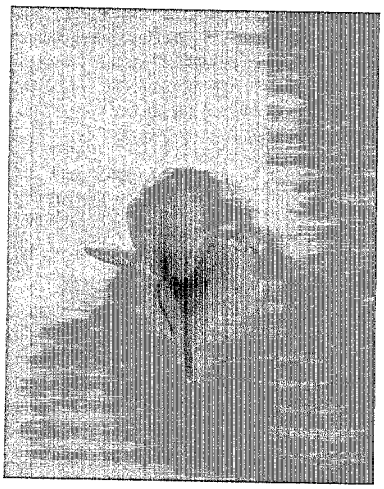
Figure 5:
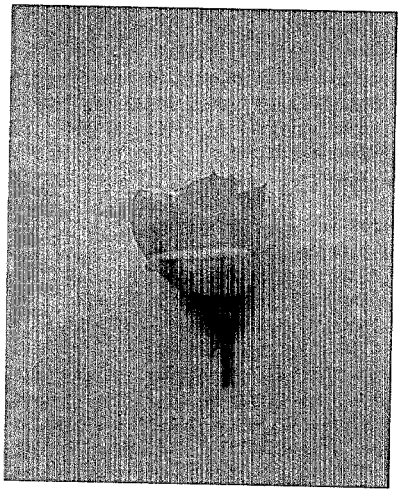
Figure 6:
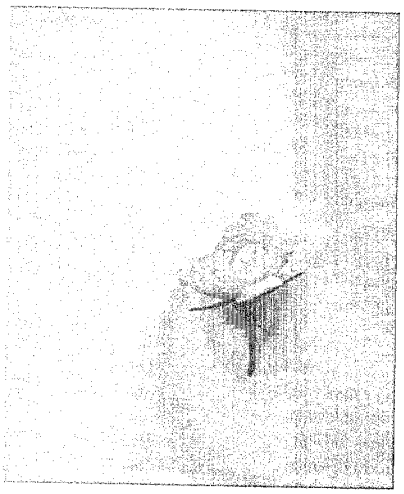
Figure 7:
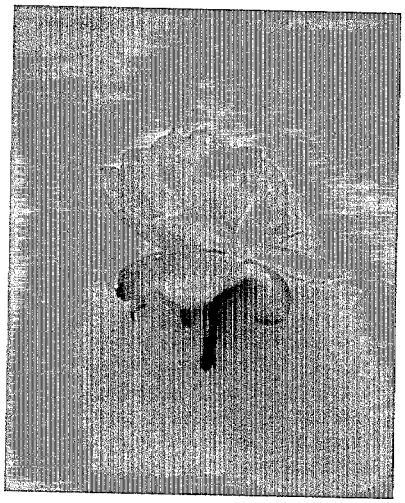
Figure 8:
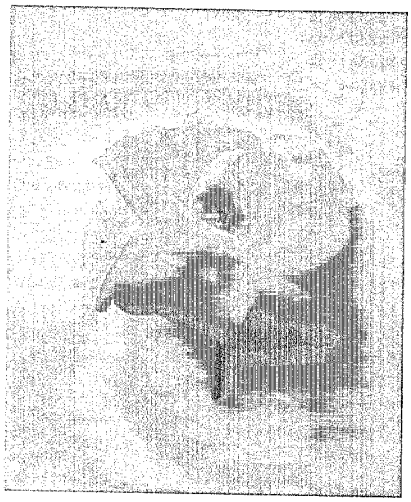
Figure 9:
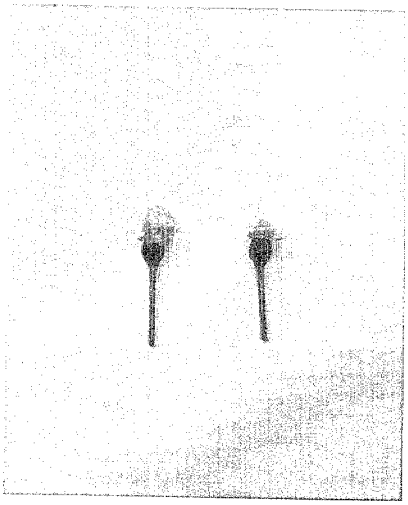
Figure 10:
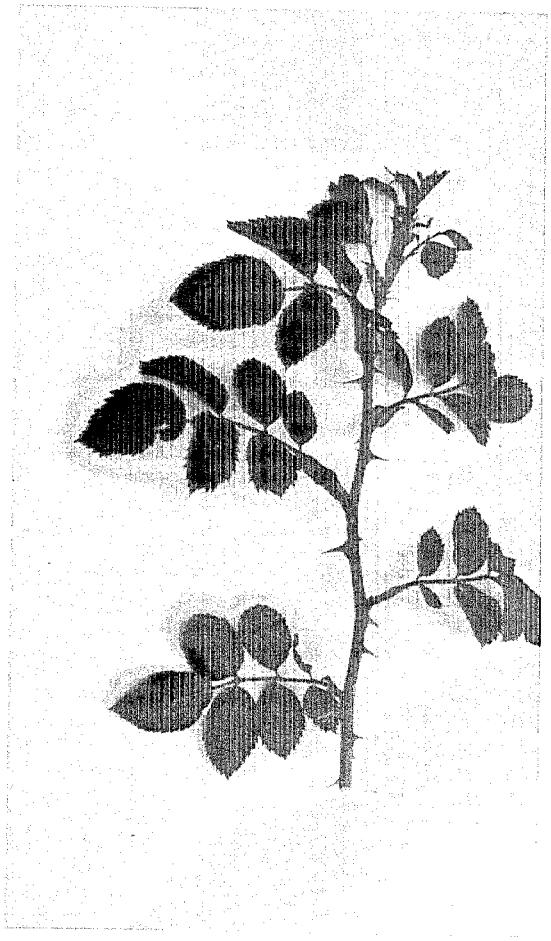
Figure 11:
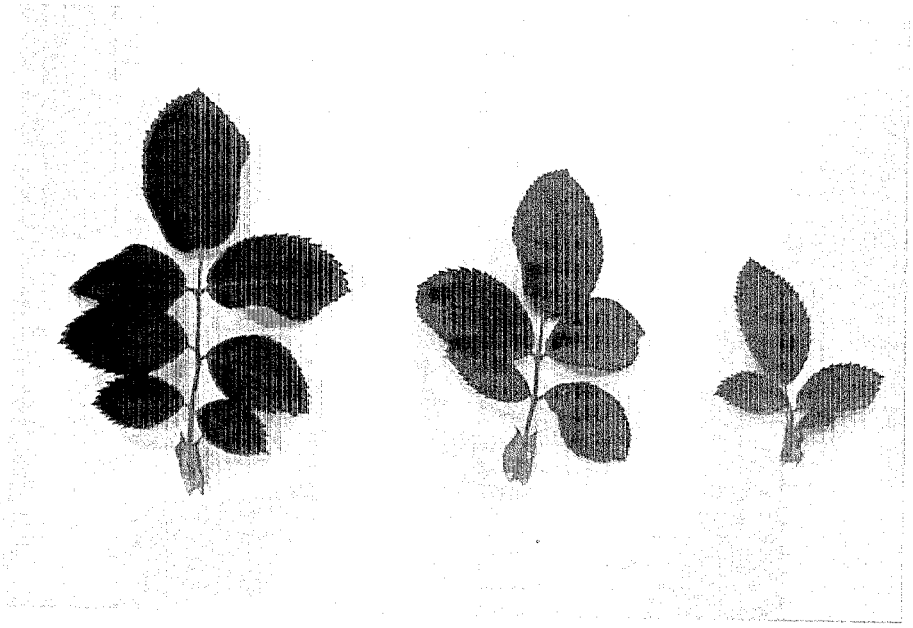
Figure 12:
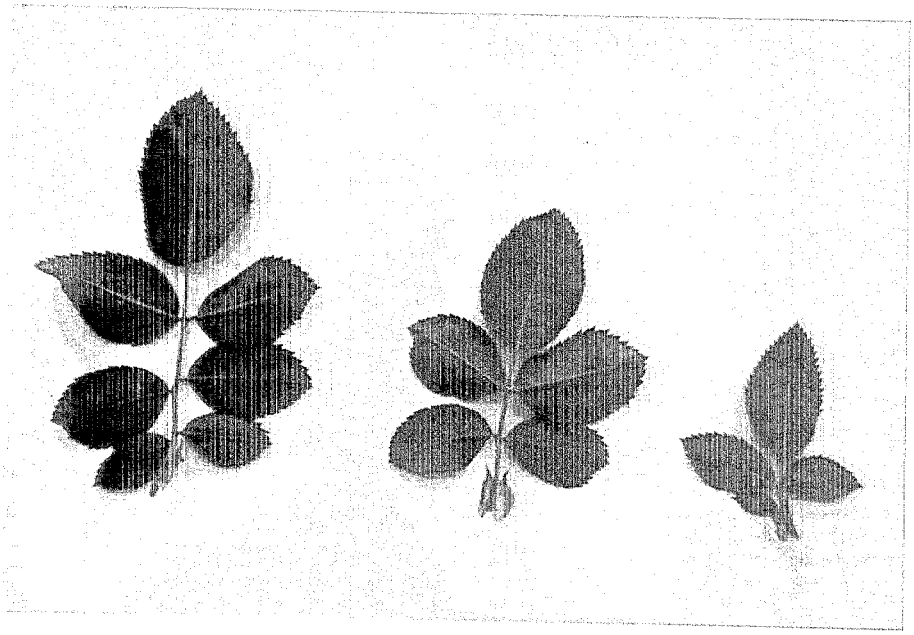

The chart used in the identification of colors is that of the Royal Horticultural Society (R.H.S. Colour Chart). Common color terms are to be accorded their ordinary dictionary significance. The description is based on the observation of 5 to 6 year-old plants of the new variety while being grown outdoors at L'Assomption, Quebec, Canada.

Class: Shrub.

Plant:

*Height.*—Approximately 1 meter on average.

*Width.*—Approximately 1 meter on average.

*Habit.*—Upright.

Branches:

*Color.*—Young stems: medium green with a tinge of red. Mature stems: light green.

*Prickles.*—Shape: slightly concave on the upper and under edges. Size: medium. Quantity: approximately 8 thorns per 100 mm of stem on average. Color: red when young and tan when mature.

Leaves: Compound and pinnate.

*Stipules.*—Fairly broad with erect auricles.

*Petioles.*—Medium green with a tinge of red when young and light green when mature.

*Petiolules.*—Very short.

*Leaflets.*—Number: commonly 3, 5 or 7. Shape: oval to rounded base, some are uneven, with acute tip. Serration: single and fairly regular.

*Color.*—Adult foliage: initially medium green approximating Green Group 137C with a red tinge on the upper surfaces and darken as the leaves mature to approximately Green Group 137A. The under surface of the leaves commonly are slightly lighter in coloration (as illustrated). Rachis: smooth with very small prickles on the underside.

Inflorescence:

*Number of flowers.*—Usually 1 to 8 per stem.

*Peduncle.*—Erect, light green with a tinge of red when young and light green when mature, prickles commonly are absent, and commonly approximately 2.5 to 3 cm. in length.

*Sepals.*—Commonly 4–5 in number, extend beyond the bud on young buds, commonly include foliation, medium green with red spots when young and light green when mature.

*Buds.*—Shape: pointed before the opening of the sepals, and progressively becoming ovoid. Color upon opening: the outer petals are deep pink, and the inner petals are pale pink.

*Flower.*—Shape: initially cup-shaped and subsequently assumes a flattened configuration (as illustrated). Diameter: approximately 8 cm on average. Color (when blooming): Roseine Purple, approaching Red-Purple Group 68B, on the upper surface, and a lighter Magnolia Purple on the under surface, approaching Red-Purple Group 70D. Some fading of the blossom coloration commonly takes place as the blossoms mature to at least Red-Purple Group 68D on the upper surface. Fragrance: slight. Petal number: approximately 20 on average. Petal texture: smooth. Lasting quality: the blossoms commonly last approximately 4 to 7 days while present on the plant under most growing conditions. Petal drop: the petals drop off fairly cleanly. Anthers: gold in coloration. Pollen: yellow in coloration. Filaments: yellow-green in coloration. Receptacle: ovoid in configuration, and turning orange red when hips are formed.

Development:

*Vegetation.*—Intermediate vigor.

*Blossoming.*—Repeat flowering from June to September.

*Hardiness.*—Survives consistently without cover in Eastern Canada (Zone 4, Quellet and Sherk, 1967).

*Resistance to diseases.*—Highly resistant to powdery mildew and blackspot.

*Preferred mode of propagation.*—The use of softwood cuttings to produce self-rooted plants is recommended for the production of quality cold-tolerant plants.

I claim:

1. A new and distinct variety of shrub rose plant characterized by the following combination of characteristics:

(a) exhibits an upright growth habit,
(b) forms on a repetitive basis attractive blossoms that are Roseine Purple on the upper surface and Magnolia Purple on the under surface,
(c) propagates well by the use of softwood cuttings,
(d) exhibits a good winter hardiness, and
(e) is particularly well suited for growing in the landscape;

substantially as herein shown and described.

* * * * *